United States Patent [19]
Zadini et al.

[11] Patent Number: 5,749,371
[45] Date of Patent: May 12, 1998

[54] AUTOMATIC GUIDEWIRE PLACEMENT DEVICE FOR MEDICAL CATHETERS

[76] Inventors: Filiberto P. Zadini, 16814 Rayen St., North Hills, Calif. 91343; Giorgio Zadini, 2237 Hilltop La., Camarillo, Calif. 93012

[21] Appl. No.: 540,197

[22] Filed: Oct. 6, 1995

[51] Int. Cl.$^6$ ............................................. A61B 5/00
[52] U.S. Cl. ......................... 128/772; 128/657; 604/164; 604/167
[58] Field of Search ........................ 128/772, 658, 128/657; 604/280, 281, 282, 164, 167, 168, 171

*Primary Examiner*—Max Hindenburg
*Assistant Examiner*—Pamela L. Wingood

[57] ABSTRACT

An improved guidewire placement device for inserting guidewires into blood vessels avoiding over-penetration or needle tip disengagement from penetrated blood vessels. Also, a device that can be universally used with any type of guidewire. The guidewire, essentially a wire helically wound in spires around at least one solid core wire, has a segment specially adapted for air sealing having a cylindrical even surface, and being interiorly sealed to passage of air. The device comprises a housing and a hollow needle connected to the housing. The housing has a guidewire chamber containing a tract of the guidewire, with its tip aligned with the needle tip, gripping means for releasably engaging the guidewire and means for self-propelled advancement of the gripping means to advance the guidewire at the proper time. The housing has also a vacuum chamber communicating with the hollow needle, and vacuum creating means to create a vacuum pressure upon insertion of the needle into the patient's body tissue. The self-propelled advancement of the guidewire is actuated either automatically as a result of change of the vacuum pressure occurring within the device upon blood vessel penetration of the needle tip, as in the fully automatic embodiments, or is manually actuated by the operator upon visualization of accelerated backflow of blood, as in the semi-automatic embodiments. Upon entry of the guidewire into the blood vessel the gripping means disengages from the guidewire to allow further advancement of the guidewire and extraction of the housing from the guidewire.

19 Claims, 10 Drawing Sheets

AUTOMATIC GUIDEWIRE PLACEMENT DEVICE FOR MEDICAL CATHETERS

BACKGROUND OF THE INVENTION

1. Field of the invention

The present invention relates to wire guided catheters and specifically to automatic means of placement of guidewires of medical catheters within the lumen of blood vessels or any other suitable body cavity.

2. Prior Art

Guidewires have been used in Medicine since 1953 when Seldinger, a Swedish Physician-Radiologist, introduced them first. Since then, the use of guidewires has tremendously expanded in many fields of Medicine: Emergency, Interventional Cardiology and Radiology, Anesthesiology, Surgery, Critical Care Medicine and others.

The Seldinger technique of insertion of guidewires into blood vessels is a manual, multistep, operator-dependent procedure which has remained essentially the same for over forty years.

The Seldinger technique of insertion of guidewires into blood vessels is carried out as follows: the operator penetrates the skin of a patient with the tip of a hollow needle usually connected to a syringe in an area of an expected blood vessel location, usually a central vessel, i.e. a non visible nor palpable vessel deeply located into the body of a patient (subclavian, internal jugular, femoral or brachial vessel). The operator searches for the vessel to penetrate with the tip of the needle and once the blood vessel penetration has been ascertained by the backflow of blood in the syringe, he, or she, after disconnecting the syringe from the needle, picks up the guidewire from the kit, feeds it through the hollow needle and advances it into the blood vessel to the desired length. Once the guidewire is properly placed into the blood vessel, a vascular catheter is slid over the guidewire into the blood vessel. The whole procedure is called "central line placement". The indications for central line placement are multiple: 1. rapid administration of fluids, medications, blood or blood products, especially in situations of emergency such as cardiac arrest or shock in which most peripheral veins collapse; 2. placement of radiological-angiographic catheters; 3. insertion of cardiac catheters, such as Swan-Ganz, Angioplasty Balloon Catheters; 4. failure to obtain vascular access by peripheral route; 5. measurement of central venous pressure, a useful parameter in assessing the volume status of a patient and in guiding fluids administration; 6. insertion of transvenous pacemakers; 7. administration of hyperalimentation solutions.

The present equipment and method of insertion of guidewires is far from satisfactory: there is in fact a significant rate of failures of insertion of guidewires into blood vessels at the very first attempt and often failures of insertions with many attempts.

Indeed, the insertion of a guidewire into a central vessel presents far greater difficulties than inserting a needle or a catheter into a peripheral vessel. A peripheral blood vessel can, most of the time, be located by visualization or by palpation. Visualization and palpation are of no help in guiding the operator in inserting guidewires because guidewires are usually inserted into the so called "central" blood vessels. Central blood vessels are located deeply in the patient's body. As such, they are completely out of sight, and are undetectable by palpation.

The only locating parameter of central blood vessels is the operator's anatomical knowledge of the probable location of the vessel. For that reason, insertion of a guidewire into a central vessel is called a "blind procedure". In addition to the characteristic of being undetectable by visualization and palpation, most central blood vessels, unlikely peripheral blood vessels, are usually surrounded by or in close anatomical relation with organs or structures of vital importance such as major arteries, lungs, pleural cavities, etc. which, if injured, may cause severe complications. Indeed numerous are the complications of the Seldinger technique of guidewire insertion: hematoma formation, pneumothorax, haemo-pneumothorax, thrombosis, arterial puncture, cellulitis, phlebitis, nerve transection, nerve puncture, chylothorax Repeated attempts account for the majority of the complications associated with central vessel guidewire placement.

Experience has taught that although a number of causes can explain failures of insertion of a guidewire into a central blood vessel, a single cause is responsible for nearly all the failures of guidewire insertion with the conventional Seldinger technique of insertion: such cause is the loss of the needle tip engagement from the lumen of the blood vessel before the guidewire tip enters the blood vessel.

The maintenance of the needle tip engagement in the lumen of the blood vessel until the guidewire tip enters the blood vessel is therefore the key issue in all guidewire placements procedures.

Maintenance of the engagement of the needle tip within the lumen of the blood vessel is by no means granted with the needle tip penetration of the blood vessel. On the contrary, the engagement of the needle tip within the lumen of the blood vessel is an absolutely precarious and unstable situation which tends to further deteriorate in proportion of the time that elapses between the needle tip penetration into the blood vessel and the entry of the guidewire tip into the vessel.

Such time delay between needle tip penetration of the blood vessel wall and the entry of the guidewire tip into the blood vessel lumen, is unavoidable in the Seldinger technique of insertion. Indeed, as above described, between the needle penetration of the blood vessel and the actual insertion of the guidewire into the vessel lumen, the operator has to complete numerous procedural steps. Due to the unavoidable delay of guidewire entry into the blood vessels, inherent with the Seldinger technique, the chances of successful guidewire insertion decrease significantly with the elapsing of time: the longer is the delay from the needle penetration of the blood vessel until the actual insertion of the guidewire into the vessel lumen, the less are the chances of successful placement of the guidewire into the interior of the blood vessel.

To obviate to the problems encountered with the present manual multistep technique of guidewire insertion into blood vessels, Zadini et Al. disclose in U.S. Pat. No. 5,415,177 a guidewire placement device for intravascular catheters comprising a guidewire, a hollow needle and self-propelled means for inserting the guidewire into the blood vessel upon penetration of the wall of the blood vessel by the needle tip.

In the device disclosed by Zadini et Al. the guidewire tip is assembled in a position of near alignment with the needle tip. A vacuum is created within the device after needle insertion into the skin overlaying a blood vessel. The needle is then advanced toward an expected location of a blood vessel. Upon entry of the needle tip into the blood vessel, the vacuum within the device accelerates a backflow of blood from the blood vessel into the device.

In the automatic version of the Zadini et Al. device the vanishing of the vacuum caused by the backflow of blood triggers the advancement of the guidewire into the blood vessel by the self-propelling means. Due to the near alignment of the guidewire tip with the needle tip, the entry of the guidewire tip into the blood vessel occurs immediately, without delays, upon needle penetration of the blood vessel.

In the semi-automatic version, the self-propelling means actuated manually by the operator upon visualization of backflow of blood within the device. While the blood is being withdrawn, ascertaining the operator of the proper location of the needle tip within the lumen of the blood vessel, the operator actuates the advancement of the guidewire by releasing the self-propelling means. Such release may occur by pressing of a trigger or by further withdrawal of the vacuum creating means. Being the tip of the guidewire aligned with the tip of the needle, the entry of the guidewire tip into the blood vessel occurs nearly instantaneously without delays upon actuation of the self-propelling means by the operator.

Virtually all the drawbacks of guidewire insertion observable with the manual Seldinger technique are eliminated with the Zadini's automatic guidewire placement device. As described above, in the Zadini's device the loss of engagement of the needle tip from the blood vessel before entry of the guidewire tip into the vessel is virtually impossible.

The Zadini's guidewire placement device is however more apt to insert solid guidewires or guidewires wherein the spires are rather tightly in contact among themselves and tightly in contact with the guidewire core to allow negligible passage of air inside the guidewire or teflon coated guidewires. With guidewires where the spires are somewhat loosely encircling the core or are not tightly contacting one to another, a slow air leakage may occur between spires or between guidewire core and spires, and said slow air leakage may limit the length of time the vacuum can be retained within the vacuum chamber of the Zadini's device. The amount of such air leakage can vary from guidewire to guidewire, and consequently the duration of retention of vacuum may also vary depending upon the type of guidewire used, making the procedure of automatic guidewire placement by the Zadini's device a procedure dependent from the type of guidewire used and from the time required to locate and enter the vessel with the needle. In fact, searching for a blood vessel by the operator in an area of expected blood vessel location may at times be time consuming regardless of the technique being used, and in those particular cases the device disclosed by Zadini et Al. the vacuum in the Zadini's device may not be maintained long enough for the time needed to find the vessel, and may be required that the device is rearmed, i.e. that vacuum is created again within the device, and, for that purpose of re-creating the vacuum, the needle needs to be extracted from the skin, and the operation of skin insertion is repeated.

These problems inherent to the Zadini's device can be eliminated with the improved automatic guidewire placement device which is proposed here below.

Brief Summary of the invention

With the present invention an improved automatic guidewire placement device is proposed which can be universally used for every type of guidewire regardless that its spires are loosely encircling the core or tightly in contact with it and regardless that its spires are tightly in contact among themselves or in loose contact, and regardless of the fact that the guidewire core is single or made of multiple strands bunched together, or that has any other special feature. Regardless of the type of guidewire which needs to be used, the improved automatic guidewire placement device here proposed invariably allows the operator to extend near indefinitely the time of blood vessel search without the need for possible repeated rearmings and reutilizations of the device.

With the present invention an improved automatic guidewire placement device is proposed comprising a housing in flow communication with a hollow needle, the housing having a vacuum chamber to retain a vacuum pressure, the vacuum chamber having a sealing member sealingly engaging a guidewire having a segment that engages the sealing member adapted for the purpose of hermetically maintain the vacuum pressure within the vacuum chamber.

A guidewire thus modified has also the important advantage of preventing unwanted injection of air into the blood vessel upon the first stage of advancement of the guidewire into the vessel. Such injection of air into the blood vessel can cause air embolism possibly resulting in morbidity to the patient.

For the purpose of preventing air embolism, the device may also be provided with an opening formed in the chamber which houses the guidewire and the self-propelling means.

DETAILED DESCRIPTION OF THE INVENTION

Figure 1:
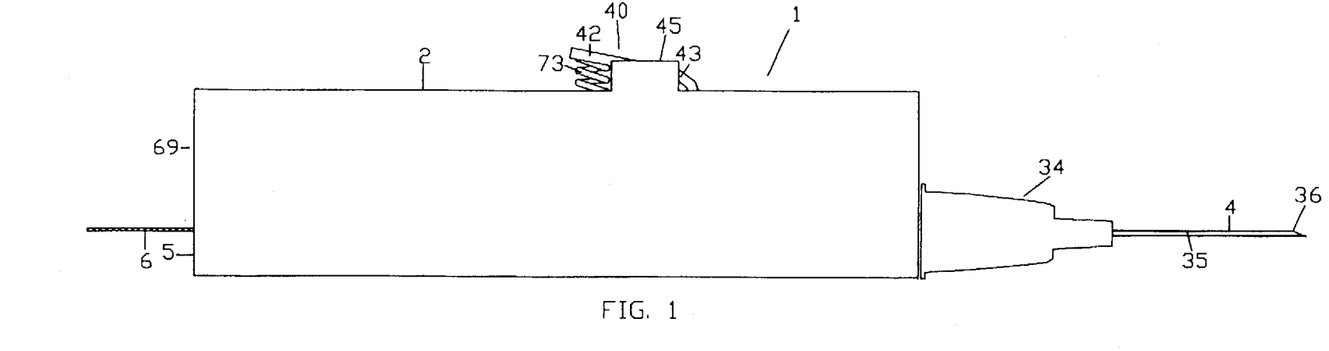
FIG. 1 is side view of the automatic guidewire placement device.
Figure 2:
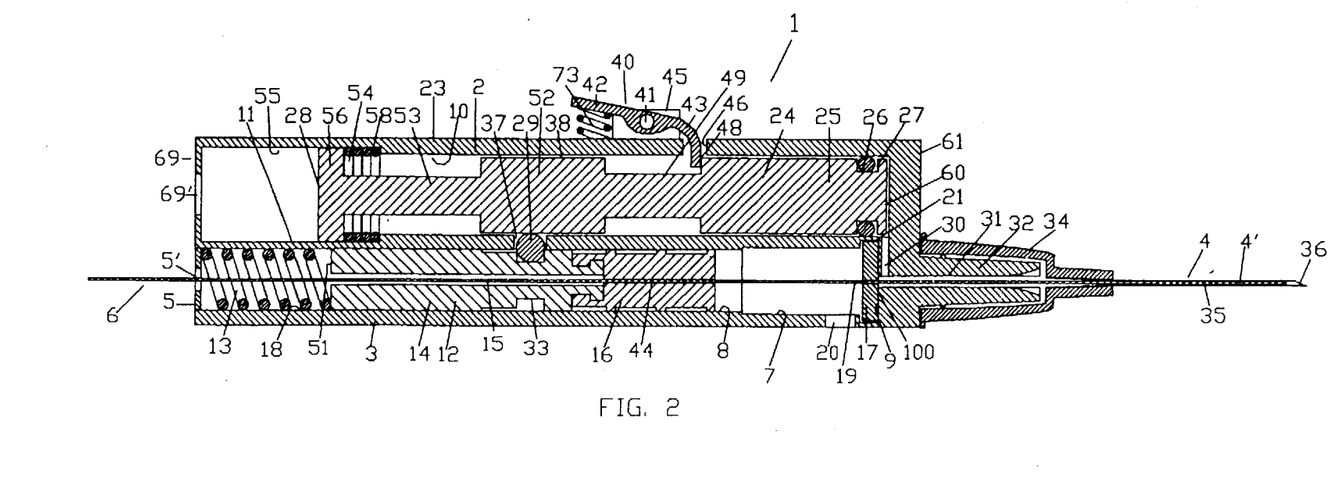
FIG. 2 is a cross sectional view of the automatic guidewire placement device at rest, prior to use along the longitudinal axis.

A typical embodiment, fully automatic, of the Automatic Guidewire Placement is illustrated in FIGS. 1 to 7. FIG. 1 is a side view of the device, generally indicated by 1, prior to use. The device is composed of three main parts: a housing 2, a needle 4 and a guidewire 6. As shown in FIG. 2, which is a cross sectional view of the device of FIG. 1, housing 2 is composed of two parallel chambers of generally cylindrical shape: guidewire chamber 8 and vacuum chamber or vacuum means 10, separated longitudinally by divider wall 11.

Guidewire chamber 8, delimited laterally by side wall 3, posteriorly by posterior wall 5 and anteriorly by anterior wall 9, has a posterior segment 18 and an anterior segment 7 of larger diameter and shorter length than posterior segment 18.

Within guidewire chamber 8, guidewire piston 12 is slideably mounted. Guidewire piston 12 is composed of a posterior segment 14 and an anterior segment or guidewire introducer or guidewire gripping/releasing means 16 made of resilient compressible/expandable material such as rubber. Guidewire introducer or guidewire gripping/releasing means 16 could also be designed as a mandrel 160 shown in FIG. 4 or as a chuck not shown.

Figure 4:
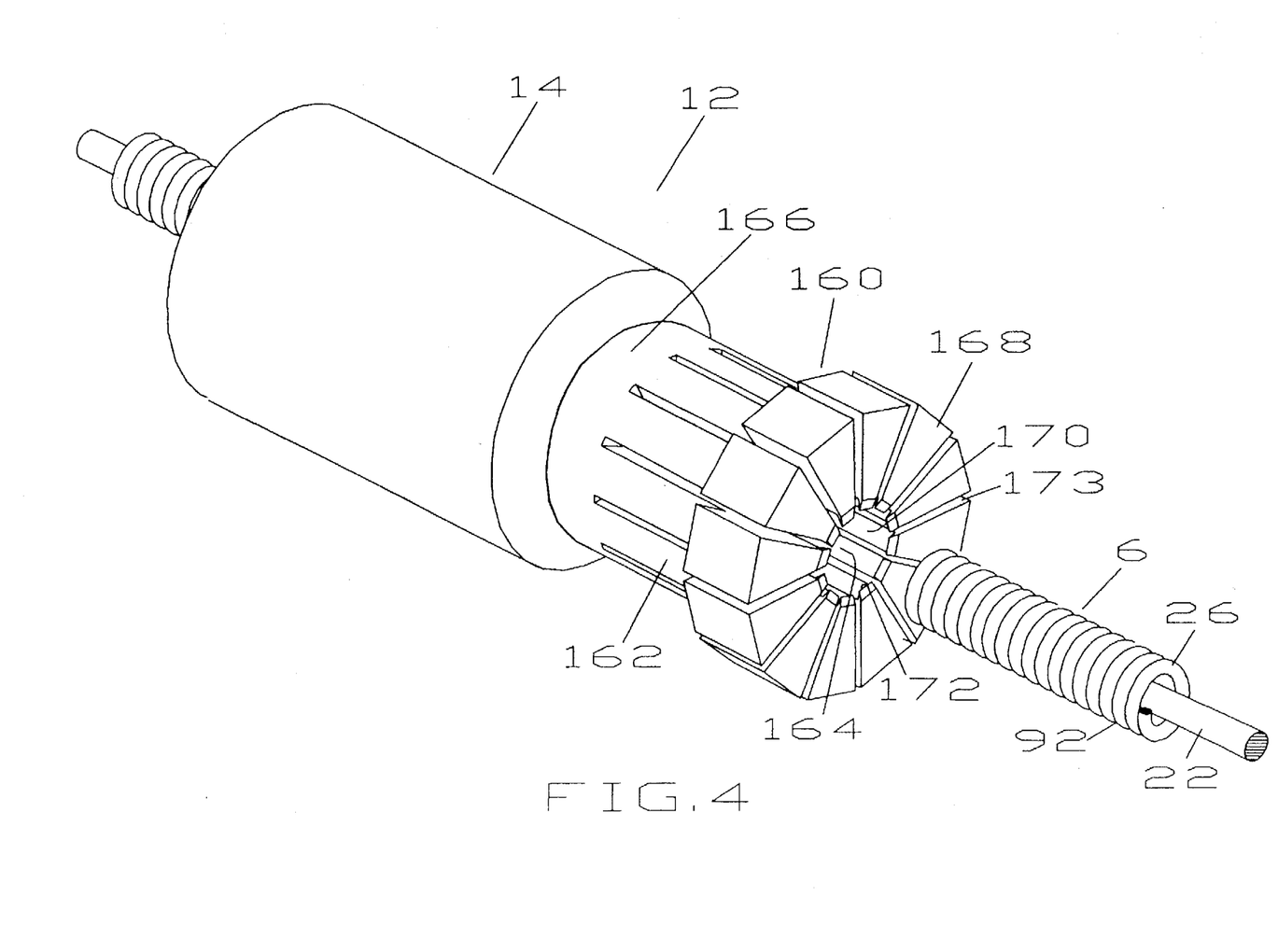
FIG. 4 is a perspective view of an alternative form of the gripping/release mechanism for guidewires shown in FIG. 1, specifically a modified mandrel.

Mandrel 160 is a grossly cylindrical piston like structure positioned in front of piston 14 and attached to it. It is formed with multiple resilient gripping elements 162 separated by slits 173, said gripping elements 166, protruding from mandrel base 166, having gripping heads 168, equidistant from the longitudinal axis of mandrel 160 to form bore 164. With the device in position of rest prior to use guide wire 6 is engaged and clamped at the center of mandrel 160, along its bore 164, by gripping heads 168 of elements 162, constricted centripetally by the rigid side walls 3 of chamber 18 around guidewire 6.

Elements 162 of mandrel 160 shown in FIG. 4, or a chuck, may have an even internal surface 170 or, better, a rough internal surface 170 to reduce the chances of sliding of guidewire 6 in respect to mandrel 160 or to a chuck, as it will be explained below in the description of the operations. Elements 162 of mandrel 160 can be better designed, as better shown in FIG. 5, as having a series of parallel ridges 172 fitting into correspondent depressions 92 between spires 26 of guidewire 6 when mandrel 160 or the chuck tightened around the guidewire in position of rest.

Figure 5:
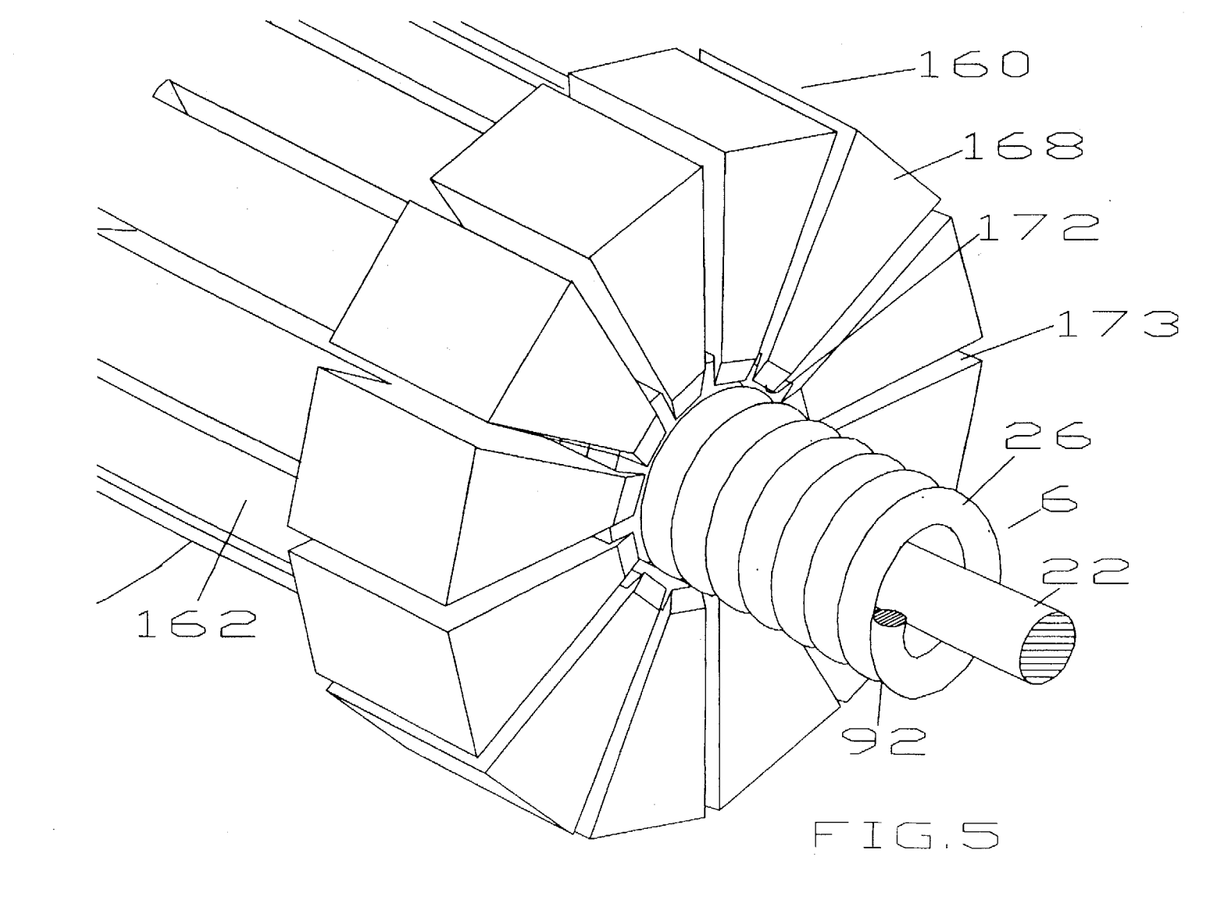
FIG. 5 is an enlarged view of a portion of the mandrel of FIG. 4.

Ridges 172 of mandrel 160 or chuck do not have to be numerous. In fact a single ridge 172 fitting into a depression 92 between spires 26 of guidewire 6 could be sufficient. Parallel ridges 172 of mandrel 160 or of a chuck warrant an optimal gripping on guidewire 6, totally independent from the degree of tightening force exerted upon guidewire 6 by elements heads 168 of mandrel 160 or the jaws of a chuck.

Spring or resilient means or self-propelling means 13 is mounted within posterior chamber segment 18 of guidewire chamber 8, posteriorly to posterior piston segment 14 of piston 12, and seats between posterior face 51 of posterior piston segment 14 of piston 12 and posterior wall 5 of guidewire chamber 8. Posterior wall 5 of guidewire chamber 8 has opening 5' for guidewire 6. Posterior segment 14 of guidewire piston 12 has, at its center, axial tract 15 for guidewire 6 which is mounted in a slideable fashion within axial tract 15. Guidewire introducer 16, as shown in FIG. 2, in position of rest prior to use, is compressed within posterior narrower chamber 18, and, by such compression, tightens in a gripping fashion around guidewire 6 which is mounted within passageway 44 of guidewire introducer 16.

Sealing member or sealing means 17 is sealingly engaged to, and seats on, annular recess 21 formed within anterior wall 9 of guidewire chamber 8 and provides sealing around guidewire 6 within passageway 19 located at the center of sealing member or means 17. Guidewire 6, although, as pointed out above, is sealingly engaged to sealing member 17, remains slideable along passageway 19 of sealing member or means 17.

For the purpose of obtaining a sealing, between guidewire 6 and sealing member 17, capable of being maintained indefinitely or reliably for the time required to locate the vessel even in cases when such time is extended for difficulties in locating the vessel, guidewire 6 is modified in segment 100. As better seen in FIG. 3, the modified segment 100 of guidewire 6 is cylindric with an outer diameter which is about the same as the outer diameter of guidewire 6 and has a substantially even surface for sealingly and slideably engaging the sealing member 17 of vacuum chamber 8. As better seen in FIGS. 3A, 3B, 3C and 3D the cylindric segment is interiorly closed to passage of air.

Figures 3, 3A, 3B:
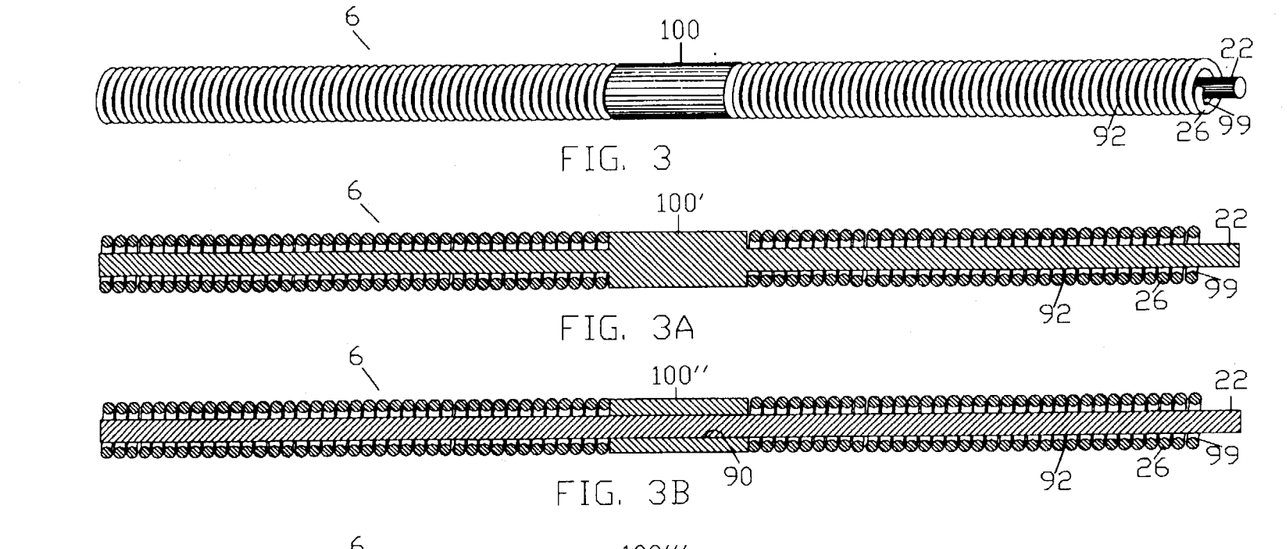
FIG. 3 is an enlarged view of the guidewire, showing a modified segment.
FIGS. 3A, 3B, 3C and 3D are cross sectional views of various type of a modified segment of the guidewire.

Modified guidewire segment 100' of FIG. 3A, which is a cross section view of guidewire 6 of FIG. 3, is designed as an enlarged solid cylindrical segment of guidewire core 22, interposed between series of spires 26 of guidewire 6, being 92 the space between core 22 and spires 26.

FIG. 3B, is a cross sectional view of another embodiment of modified segment 100. In this embodiment, modified segment 100" is designed as a cylinder with axial bore 90 for sealingly engaging guidewire core 22.

Figures 3C, 3D:
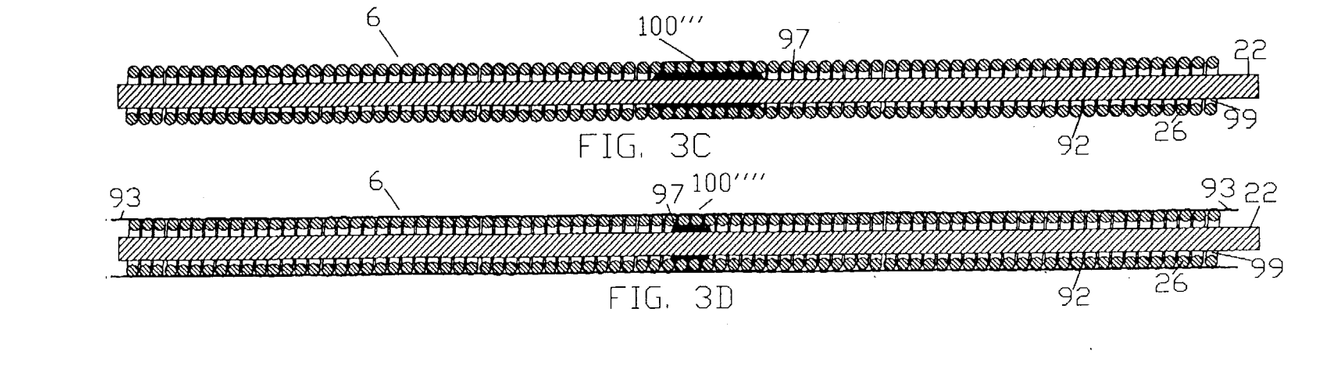

In modified guidewire segment 100''' of FIG. 3C, which is a cross sectional view of yet another embodiment of guidewire 6, space 92 between core-wire 22 and spires 26 and space or depression 92 between spires 26 are filled with sealing material such as plastic or metal to airtightly cement spires 26 and core guidewire 22 together. Outer surface 27 of guidewire segment 100''' is also leveled between spires 26 to obtain a smooth cylindrical surface for proper sliding of the guidewire along passageway 19 of sealing member 17.

In guidewire 6' of FIG. 3D, the guidewire has an airtight tubular coating 93 of material such as teflon having a segment, 100'''', sealed to passage of air along the interior of said tubular coating.

Window 20 in device 1 is formed inferiorly and anteriorly in wall 3 of anterior segment 7 of guidewire chamber 8 to permit the exit of air from anterior segment 7 of guidewire chamber 8 during the operation, as it will be described below in the description of the operation.

Vacuum chamber 10 of general cylindrical shape is delimited laterally by side wall 23, anteriorly by anterior wall 61, posteriorly by wall 69, being 69' the opening in posterior wall 69. Within vacuum chamber 10, vacuum creating means or piston 24 is mounted in slideable fashion. Piston 24 is composed of head 25, body 52 and posterior segment 53. Posterior segment 53 has flange 56. Piston 24 is urged backwardly by spring 54 seating in annular recess 55 formed within side wall 23 of vacuum chamber 10 between flange 58 of annular recess 55 and flange 56 of posterior piston segment 53. Piston head 25 has sealing O- ring 26 seating on annular recess 27, to provide sealing between vacuum creating means or piston 24 and lateral wall 23 of vacuum chamber 10. Piston 24 has a posterior wall 28 and side wall 38. Space 60 is the space within chamber 10 in front of piston head 25. Ball 29 is engaged in window 37 of divider wall 11 and seats inferiorly on annular recess 33 of posterior segment 18 of piston 12, and it is prevented superiorly from being dislodged from window 37 by side wall 38 of vacuum creating means or piston 24. In position of rest of device 1, prior to use, ball 29 locks piston 12 urged forward by spring 13 not allowing its anterior displacement.

Figure 6:
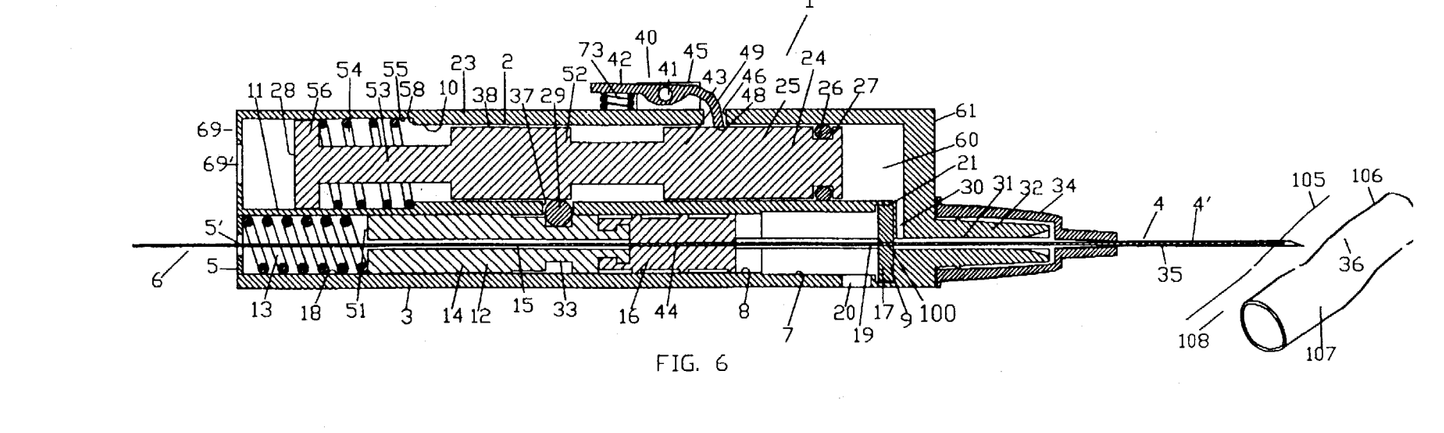
FIG. 6 is cross sectional view of the device of FIG. 1 shown in use, after skin penetration by the needle tip of the device but prior penetration of a blood vessel.

As shown in FIG. 2 and better in FIG. 6, space 60 of vacuum chamber 10 in front of piston 25 communicates via conduit 30 formed within anterior wall 9 of guidewire chamber 8 with passageway 31 in nozzle 32 of housing 2, said nozzle 32 protruding forwardly from the anterior lower aspect of housing 2. As shown in FIG. 2 lever 40 is mounted in mounting bracket 45 via pin 41. Trigger or lever 40 is composed of upper arm 42 and lower arm 43. In position of rest prior to use lower arm 43 of lever 40, forwardly and downwardly tilted by spring 73, locks vacuum creating means or piston 24 by engagement of tooth 48 of lower arm 43 of lever 40 with annular recess 49 of vacuum creating means or piston 24 through opening 46 formed in side wall 23 of vacuum chamber 10. Piston 24 is therefore maintained in an advanced position with the device at rest prior to use.

Needle 4 is composed of needle shaft 35, needle hub 34 which seats circumferentially on nozzle 32 of housing 2, and needle tip 36. Needle 4 has lumen 4'. As shown in FIG. 2 guidewire 6 is slideably mounted from front to back within lumen 4' of needle 4, passageway 31 within nozzle 32, passageway 19 within sealing member or means 17, passageway 44 within guidewire introducer 16, axial tract 15 within piston 12, and exits posteriorly from posterior end 51 of piston 12 and finally through opening 5' of guidewire piston chamber 8 to continue posteriorly outside of device 1.

Description of the operation

As seen in FIG. 6, skin 105 is penetrated with needle tip 36 of needle 4 in an area overlaying central vessel 107 or any other suitable body cavity where the guidewire is intended to be placed. Please refer to FIG. 6 for the anatomy of the body area, being 105 the skin ,108 the subcutaneous tissue, 107 the blood vessel and 106 the blood vessel wall. As soon as needle tip 36 is well under skin 105, in subcutaneous tissue 108, the operator acts upon lever or trigger 40 by pressing downward upper arm 42 of trigger 40. Piston 24, no longer retained by tooth 48 in annular recess 49, is moved backwardly by spring or resilient means 54.

Posterior displacement of vacuum creating means or piston 24 creates a vacuum in front of piston head 25 in space 60 within vacuum chamber 10. Posterior displacement of piston 25 caused by resilient means 54 after skin penetration and consequent sealing needle tip 36 is only of a small amount due to the resistance opposing the further posterior displacement of vacuum creating means or piston 24, such resistance being caused by the vacuum being created in space 60 in front of vacuum creating means or piston 24.

Due to hermetic sealing between sealing member 17 and modified guidewire segment 100 as above described, vacuum pressure in space 60 in front of vacuum creating means or piston 24 will be maintained at length permitting a near indefinite search for the vessel.

Figure 7:
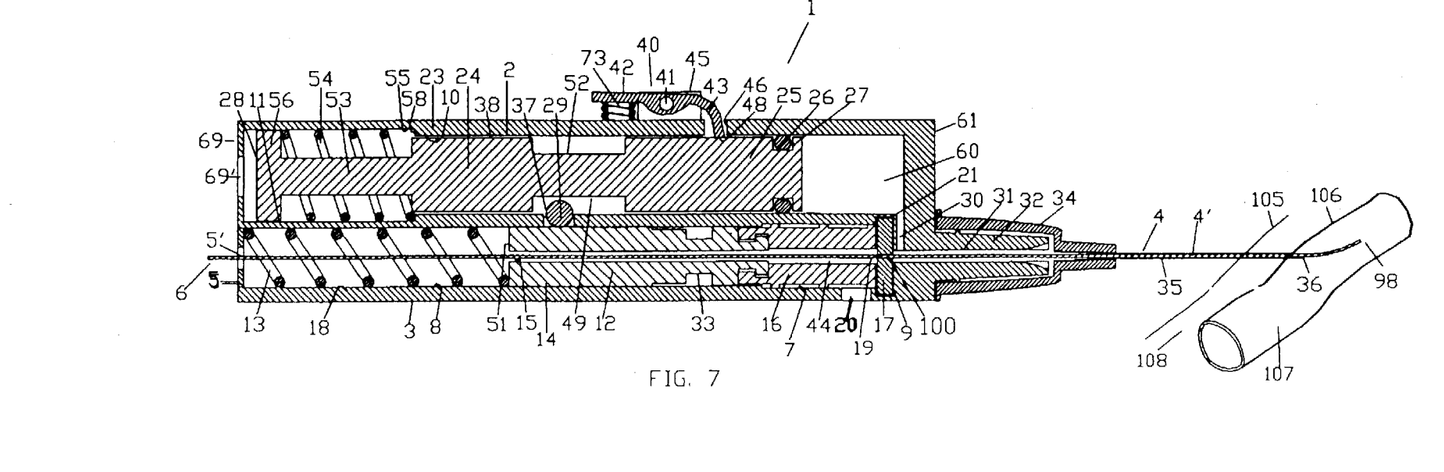
FIG. 7 is cross sectional view of the device of FIG. 1, after penetration by the needle tip of the device of the blood vessel, with the guidewire advanced within the lumen of the blood vessel.

As shown in FIG. 7, as soon as needle tip 36 penetrates a central blood vessel 107, such as for instance a femoral vein or artery, by perforating its wall 106, blood backflow occurs in an accelerated fashion into vacuum chamber 10 in front of piston head 25, the blood rushing into space 60, passing through conduit 30. The backflow of blood causes a near sudden vanishing or decrease of the vacuum pressure created in the prior stage in space 60 in front of piston head 25 of vacuum creating means or piston 24 within vacuum chamber 10. Such vanishing of the vacuum or decrease of the vacuum pressure will not retain vacuum creating means or piston 24 any longer in the advanced position above described, allowing full posterior displacement of vacuum creating means or piston 24 by spring 54. Air is expelled posteriorly via opening 69' of posterior wall 69 of vacuum chamber 10 not opposing so any resistance to posterior displacement of vacuum piston 24. Ball 29 will be ejected, forced out from recess 33 of piston 12' by the advancement of piston 12', due to the fact that the equator of ball 29 is above the lower edge of window 37. Ejection of ball 29 occurs upon alignment of both recesses 49 of piston 24' and 33 of piston 12'. Ejection of ball 29 can be facilitated by a slanting of the posterior edge of recess 33. Upon dislodgment of ball 29 from annular recess 33 of piston 12, piston 12 is free to advance being urged forwardly by spring 13. Guidewire introducer or anterior guidewire piston segment 16, being advanced as part of piston 12, will carry forward guidewire 6 due to the gripping action of guidewire introducer 16, tightened around guidewire 6 along passageway 44 of guidewire introducer 16 while sliding within posterior segment 18 of guidewire chamber 8, of smaller diameter than anterior segment 7 of guidewire chamber 8. As soon as guidewire introducer 16 enters anterior segment 7 of guidewire chamber 8, guidewire introducer 16, made, as above described, of resilient material, will be able to expand in anterior segment 7 of guidewire chamber 8, being anterior segment 7 of larger diameter than guidewire chamber posterior segment 18 releasing the grip on guidewire 6 which will stop to advance. Release of guidewire 6 from the grip of introducer 16 allows further manual advancement of guidewire 6 and extraction of device 1 from guidewire 6. Advancement of guidewire 6 can be also accomplished by mandrel 160 in place of guidewire introducer 16. As shown in FIG. 5 elements 162 of mandrel 160 grip guidewire 6 via ridges 172 fitting between depressions 92 between spires 26 of guidewire 6 within guidewire posterior chamber 18. As per guidewire introducer 16, as soon as mandrel 160 enters anterior segment 7 of guidewire chamber 8, elements 162 of mandrel 160, made, as above described, of resilient material, will be able to expand in anterior segment 7 of guidewire chamber 8, being anterior segment 7 of larger diameter than guidewire chamber posterior segment 18. Ridges 172 will thus release their grip on guidewire 6 and advancement of guidewire 6 will stop and guidewire 6 is released for further manual advancement and extraction of device 1 from guidewire 6.

During advancement of guidewire introducer 16, due to the hermetic sealing between sealing member 17 and modified guidewire segment 100, air will not enter needle lumen 4' of needle 4. Also during advancement of piston 12 air will be expelled through window 20. The ejection of air through window 20 prevents introduction of air into needle lumen 4' and ultimately into blood vessel 107. For the above reasons the risks of air embolism are practically eliminated.

Presence of window 20 also eliminates any opposing pneumatic resistance to the advancement of guidewire introducer 16. Guidewire introducer 16, once fully advanced into anterior segment chamber 7 of guidewire chamber 8, releases completely the grip on guidewire 6, which becomes free to be slid in both directions, forwardly and backwardly, by the operator's hands along and within hollow needle 4, passageway 31 of housing nozzle 32, passageway 19 of sealing member of means 17, passageway 44 of guidewire introducer 16, axial tract 15 of guidewire piston 12.

Once guidewire tip 98 is engaged in blood vessel 107, the insertion of the guidewire into blood vessel 107 is secured. Further advancement of the guidewire can be carried out by the operator either by first extracting the device out of the guidewire, and then by manually advancing the guidewire fully into position, or by first fully advancing the guidewire through the device into the blood vessel, and then extracting the device. In this second option, after the critical initial advancement is carried out by introducer 16, resulting with engagement of tip of guidewire 98 into blood vessel 107, partial or full advancement of guidewire 6 into the blood vessel 107 can be not only manually achieved as described, but can also be accomplished by resilient means which can propel guidewire 6 further into blood vessel 107 to any desired length.

Figure 8:
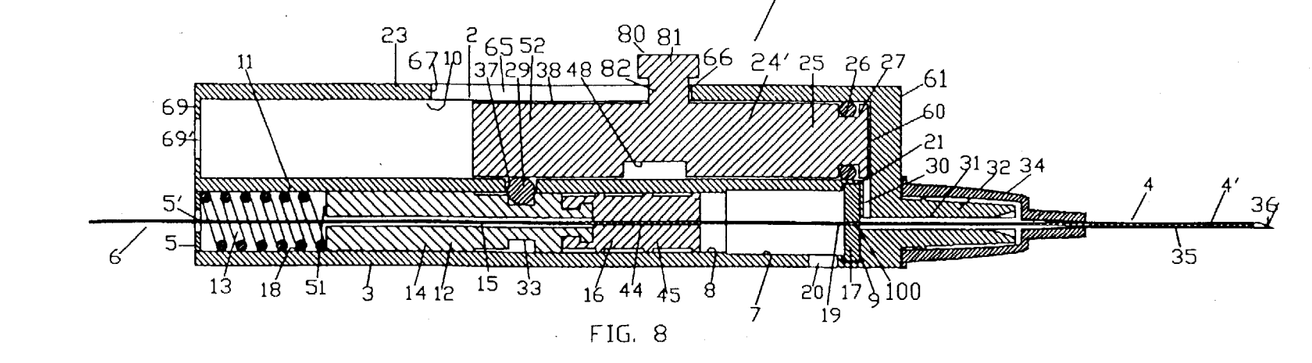
FIG. 8 is a cross sectional view of another version, semiautomatic, of the device of FIGS. 1 to 7, shown prior to use.

FIG. 8 shows an alternative form, semiautomatic, of device 1 described in FIGS. 1 to 7, generally indicated at 1'. Mainly, this is an embodiment where vacuum is created manually by withdrawing piston or plunger or vacuum creating means 24' and where spring or resilient means or self-propelling means 13 is triggered manually by further withdrawal of plunger or piston or vacuum creating means 24'.

The device is basically the same as the one described in FIGS. 1 to 7 except for the few differences outlined below. Spring or resilient means 54 and lever 40 are no longer present. Side wall 23 of vacuum chamber 10 is formed superiorly with slit 65 having front end 66 and posterior end 67. Piston 24' is provided with handle apparatus or means 80 slideable through slit 65 as it will be explained below in the description of the operation. Handle means 80 is composed of handle 81 and arm 82 connected to body of vacuum creating means or piston 24'. Arm 82 of handle 80 is slideable along slit 65. Handle apparatus 80 permits the sliding of the piston 24' by the operator acting upon said piston handle 80 as it will be described in the operation. Vacuum piston 24' is formed inferiorly with recess 48.

Vacuum piston or vacuum creating means 24' may also be designed as a piston plunger such as a syringe plunger wherein the operator withdraws the piston by pulling the plunger handle backwardly. However, the above described piston version with handle means 80 is preferable, being designed to render manual withdrawal of piston 24' via displacement of handle 80 an easy, convenient, single handed operation, while the version with the syringe plunger requires the use of both hands.

With device 1' in position of rest, prior to use, as shown in FIG. 8, ball member 29 is shown as being engaged in window 37 of divider wall 11, seating inferiorly on annular recess 33 of guidewire piston 12' and being prevented to exit superiorly through window 37 by side wall 38 of vacuum piston or vacuum creating means 24'. With device 1' in position of rest, ball 29 locks therefore piston 12' in a posterior position.

Side wall 23 of vacuum chamber 10 is preferably made of transparent material to permit visualization of the interior of vacuum chamber 10.

Description of the operation

Device 1' is operated as the previously described device 1 of FIGS. 1 to 7, except for a few differences.

Figure 9:
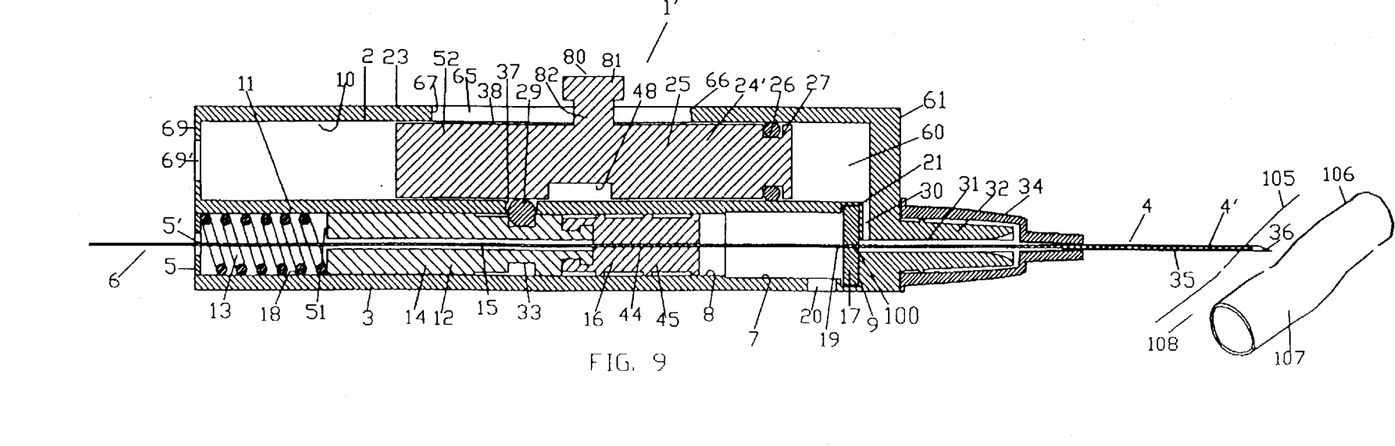
FIG. 9 is a cross sectional view of the device of FIG. 8, shown in use, after skin penetration by the needle tip of the device but prior penetration of a blood vessel.

As shown in FIG. 9, after penetration of skin 105 with needle tip 36, the operator displaces posteriorly piston 24' by sliding posteriorly handle 80. Posterior displacement of piston 24' will create a vacuum in space 60 in front of piston 24'. Posterior displacement of piston 24 will be only of a small amount due to the sealing of needle tip 36 by subcutaneous tissue 108, as the operator will sense sufficient resistance opposing the further posterior displacement of piston 24', such a resistance being caused by the vacuum being created in space 60 in front of piston 24'.

Figure 10:
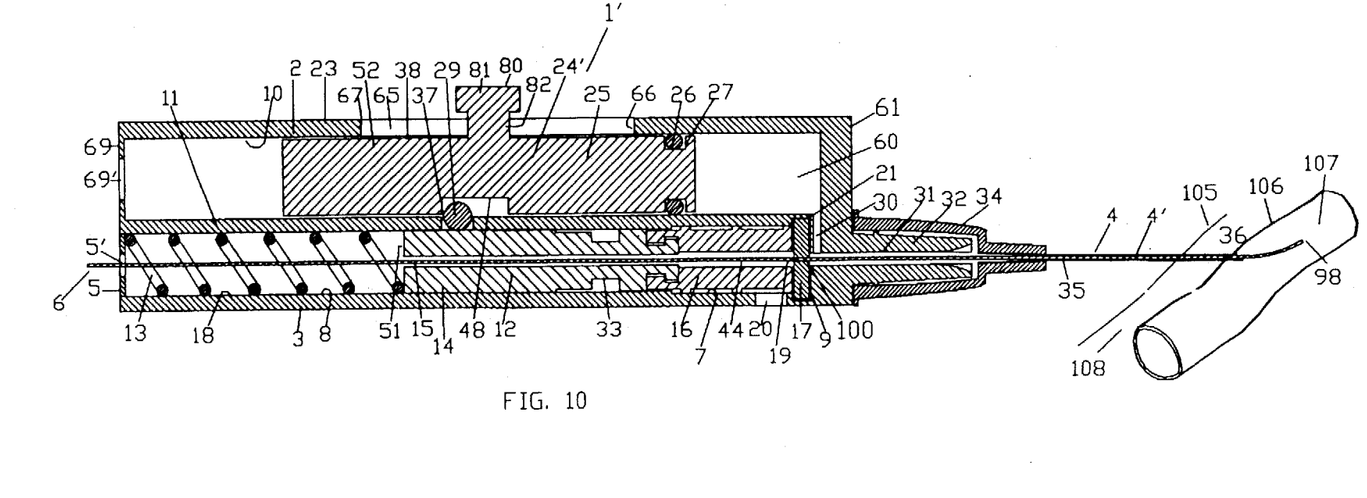
FIG. 10 is a cross sectional view of the device of FIG. 8, shown after blood vessel penetration by the needle tip of the device, illustrating guidewire advancement into the lumen of the blood vessel.

At this point the operator will search for a suitable vessel underneath skin 105 with needle tip 36 of needle 4. As shown in FIG. 10, as soon as needle tip 36 penetrates blood vessel 108, by perforating its wall 106, blood backflow will occur in an accelerated fashion into vacuum chamber 10 in front of piston 24', blood rushing into space 60 passing through conduit 30 as described for device of FIGS. 1 to 7. As soon as blood vessel penetration is ascertained by the operator visualizing blood within vacuum chamber 10 in front of piston head 25 of piston 24' or such blood vessel penetration is sensed by the operator by the fall of resistance to the continuous withdrawing force applied by the operator upon said piston 24' via piston handle 80, the operator will further displace piston 24' acting on handle 80. Posterior displacement of piston 24' results in anterior displacement piston 12' by spring or resilient means 54. Such anterior displacement of piston 12' is permitted as a result of the release/exit of locking ball 29 from recess 33 of guidewire piston 12' through window 37, occurring with the withdrawal of vacuum piston or vacuum creating means 24'. As matter of fact, ball 29 will be ejected, forced out from recess 33 of piston 12' by the advancement of piston 12', due to the fact the equator of ball 29 is above the lower edge of window 37. Ejection of ball 29 occurs upon alignment of both recesses 48 of piston 24' and 33 of piston 12'. Ejection of ball 29 can be facilitated by a slanting of the posterior edge of recess 33.

Anterior displacement of piston 12' will result in advancement of guidewire 6 into blood vessel 107 as described for the device 1 of FIGS. 1 to 7. The remainder of the operation is exactly the same as the one described for the device in FIGS. 1 to 7. With regard to the semi-automatic type, other embodiments are possible. For instance, an embodiment is possible where the vacuum is still manually created by manual withdrawal of the piston/plunger as in embodiment 1' just described in FIGS. 8 to 10, while the self-propelled means is triggered manually by manually acting upon an actuator, instead of being triggered by further manual displacement of the piston/plunger as disclosed above for device 1' of FIGS. 8 to 10. In this embodiment, as well as in the other semiautomatic embodiment, the blood needs to be visualizable by the operator when backflowing into the device by the means of making a portion of the device wall transparent to light.

Figure 11:
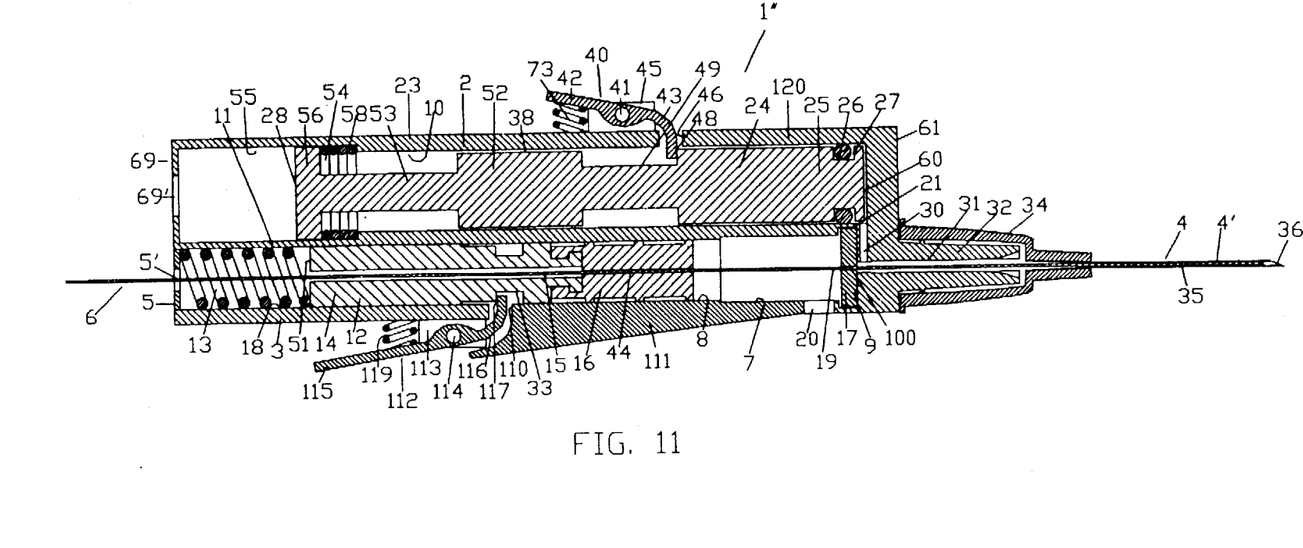
FIG. 11 is a cross sectional view of another semiautomatic version of the device of FIGS. 1 to 7, shown prior to use.

Another semi-automatic embodiment of device 1 of FIGS. 1 to 7 can be constructed, as device 1" of FIG. 11, where spring or self-propelling means 13 is manually triggered by acting upon an actuator or trigger means 112 of FIG. 11, and the vacuum is created by resilient means or spring 54 instead of being manually created by manual withdrawal of piston or plunger or vacuum creating means 24, as per FIG. 11.

Device 1" of FIG. 11, shown at rest prior to use, is basically the same as device 1 of FIG. 1 to 7, except for a few differences. Vacuum chamber 10 has at least one front segment 120 of side wall 23, said segment 120 being transparent to permit operator's visualization of the interior of vacuum chamber 10 in front of piston 25. Windows 37 of FIGS. 1 to 7 in divider wall 11 and ball 29 are no longer present. Opening 110 is formed in inferior side wall 3 of guidewire chamber 8 in front and near mounting bracket 113 for lever or trigger actuator 112. Mounting bracket 113 is mounted on inferior aspect of side wall 3 of guidewire chamber 8. Lever or trigger or actuator 112 is mounted on mounting bracket 113 via pin 114. Lever 112 has front curved arm 116 for entry into opening 110 on inferior side wall 3 of guidewire chamber 8, has tooth 117 at its free end for engagement with annular recess 33 of guidewire piston 12, and has rear arm 115 for lever actuation by the operator. Lever 112 is tilted forwardly to engage annular recess 37 via tooth 117 by spring 119. Side wall 3 of guidewire chamber 8 has inferiorly wall extension 111 to avoid inadvertent actuation of lever 112 by the patient skin when the device is operated.

The device is operated as device 1 of FIGS. 1 to 7 except that the advancement of guidewire piston 12 is actuated manually by the operator upon visualization of blood in space 60 of vacuum chamber 10, by pressing on rear arm 115 of lever or trigger 112.

Figure 12:
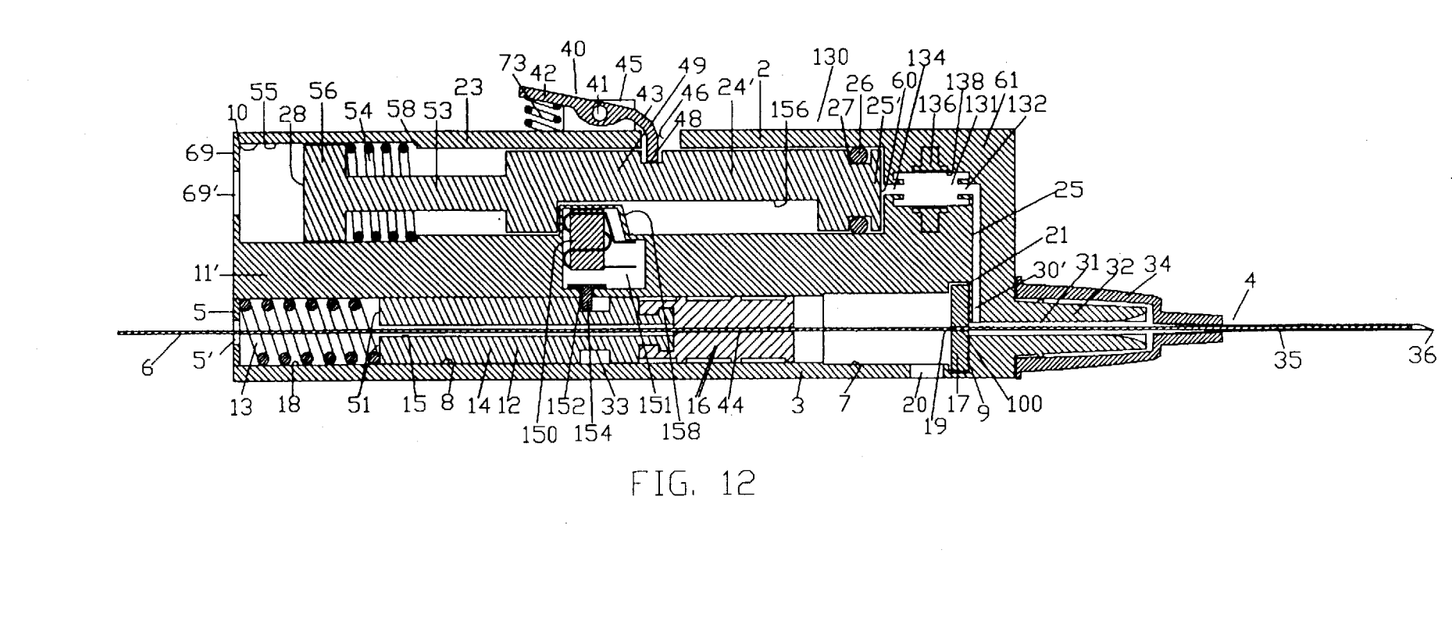
FIG. 12 is a cross sectional view showing another version, automatic, of the device of FIGS. 1 through 7.

FIG. 12 shows yet another version, fully automatic, of device 1 of FIGS. 1 to 7. The device generally indicated at 130 is basically the same as device 1 of FIGS. 1 to 5, except that blood vessel penetration by needle tip 36 of needle 4 is ascertained by opto-electric means which activates an electromagnet via a standard electric circuit. For that purpose device 130 with respect to device 1 of FIGS. 1 to 7 has the following differences.

Windows 37 of FIGS. 1 to 7 in divider wall 11 and ball 29 are no longer present. Divider wall 11' is construed thicker than correspondent divider wall 11 of FIGS. 1 to 7 for housing electromagnet 150. Also anterior wall 61' of vacuum chamber 10' is construed thicker than correspondent wall 61 of FIGS. 1 to 7 for housing blood detection chamber 131 and detection means 136.

Blood detection chamber 131 is formed within anterior wall 61' of vacuum chamber 10' and is in flow communication with conduit 30' via opening 132 and with space 60 of vacuum chamber 10' via opening 134. Opto-electric sensing means 136 is mounted within wall 61' by side walls 138 of detection chamber 10'. Side wall 138 is made of transparent material to allow passage of light.

Recess 151 is formed within divider wall 11' to house electromagnet 150 which is connected via a standard circuit to opto-electric means 136. Recess 151 protrudes into vacuum chamber 10' with recess extension 158 to house electromagnet 150. Correspondingly, piston 24" has no longer annular recess 49, but has recess 156 on its inferior aspect to adapt to presence of said electromagnet recess extension 158 of recess 151. Recess 151 has opening 152 for pin 154 which, with device 130 in condition of rest is engaged in recess 33 of piston 12, and held in that position by the side pressure exerted upon the pin by piston 12 urged forwardly by spring 13. Pin 154 is made of material responsive to electromagnetic force.

Device 130 is operated basically as device 1 of FIGS. 1 to 7, except that blood vessel penetration is senses by opto-electric means 136 sensing presence of blood within blood detection chamber 131. Presence of blood in detection chamber 131 activates electromagnet 150 via said standard electric circuit. Activated electromagnet 150 will displace pin 154 toward electromagnet 150 freeing piston 12 for advancement by spring or self-propelling means 13. As described for device 1 of FIGS. 1 to 7, advancement of piston 12 results with insertion of guidewire 6 into the blood vessel.

Figure 13A:
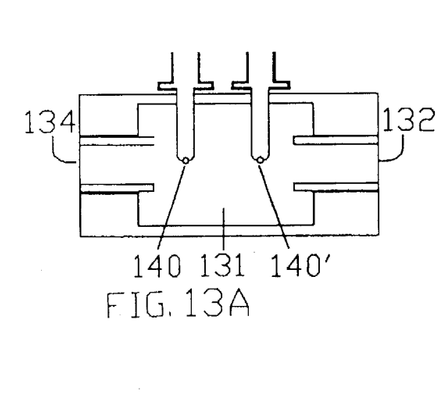
FIG. 13A is an enlarged view of the detection chamber of FIG. 12, showing in it, temperature sensors.
Figure 13B:
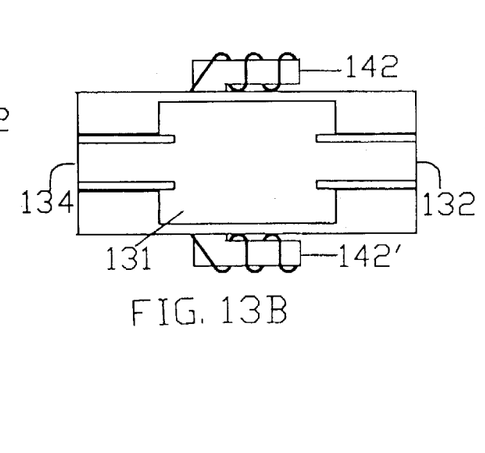
FIG. 13B is an enlarged view of a detail of FIG. 12 specifically of the detection chamber of FIG. 12, showing in it sensors detecting the electrical properties of the blood.
Figure 13C:
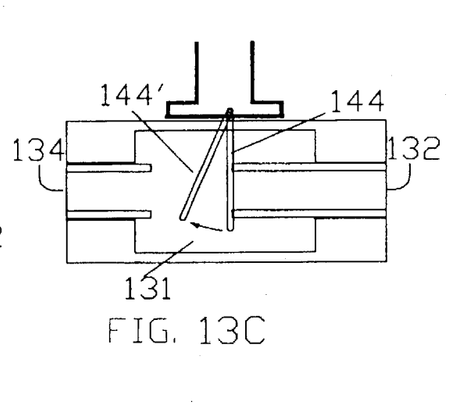
FIG. 13C is an enlarged view of the detection chamber of FIG. 12, showing in it a flow sensor.
Figure 13D:
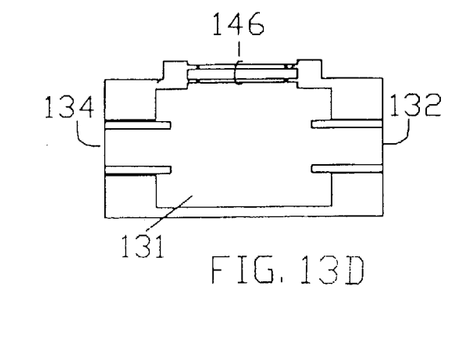
FIG. 13D is an enlarged view of the detection chamber of FIG. 12, showing in it an acoustic sensor.
Figure 13E:
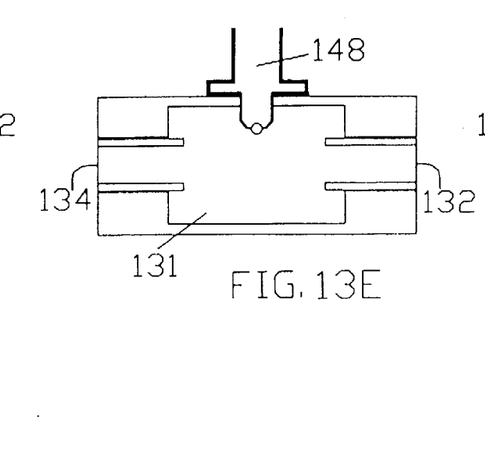
FIG. 13E is an enlarged view of the detection chamber of FIG. 12, showing in it a pressure sensor.
Figure 13F:
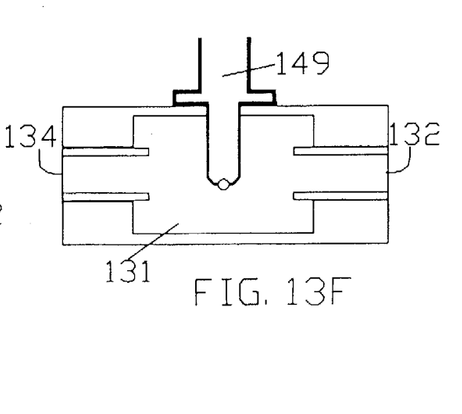
FIG. 13F is an enlarged view of the detection chamber of FIG. 12, showing in it a sensor detecting the chemical properties of the blood or its components.

Presence of blood in detection chamber 131 may be detected by various other types of sensing means, such as by temperature sensing means 140 and 140', as shown in FIG. 13A; by means 142 and 142' for sensing electric properties of the blood, as shown in FIG. 13B; means for detecting the physical property of blood as a fluid 144, shown at rest and activated, 144', as illustrated in FIG. 13C; acoustic or ultrasound sensing means 146 as shown in FIG. 13D; means for detecting chemical properties of the blood 148 of FIG. 13E and means for detecting blood components 149 of FIG. 13F.

Obviously, numerous other variations and modifications can be made without departing from the spirit of the present invention. Therefore, it should be clearly understood that the forms of the present invention described above and shown in the figures of the accompanying drawings are illustrative only and are not intended to limit the scope of the present invention.

Also, the guidewire placement device can be used to insert guidewires into body cavities other than blood vessels. Given the ability of the guidewire placement device above disclosed to insert guidewires of different types and construction, any type of guidewire can be automatically or semiautomatically inserted into any body cavity for the proper medical surgical indication.

What we claim is:

1. A guidewire placement device for insertion of a guidewire into the interior of a blood vessel comprising:
    a hollow needle,
    a vacuum chamber for vacuum pressure said vacuum chamber having means for sealingly engaging a guidewire which is slidable within said hollow needle, said guidewire having at least one segment adapted to maintain said vacuum pressure within said vacuum chamber, said vacuum pressure accelerating backflow of blood upon blood vessel penetration by said needle and
    self-propelled means for advancing said guidewire into the interior of the blood vessel upon said blood vessel penetration.

2. The device of claim 1 wherein said self-propelled means is automatically actuable upon blood vessel penetration.

3. The device of claim 1 wherein said self-propelled means is manually actuable.

4. The device of claim 1 wherein said guidewire comprises a wire helically wound in spires around at least one solid core wire.

5. The device of claim 4 wherein said segment of guidewire is cylindric with a substantially even surface for slideably engaging said sealing means of said vacuum chamber, said cylindric segment being interiorly sealed to passage of air.

6. The device of claim 4 wherein said segment of guidewire has an outer diameter substantially equal to an outer diameter of said spires.

7. The device of claim 4 wherein said segment of guidewire comprises a solid cylindrical segment having an outer diameter substantially equal to an outer diameter of said spires, said solid cylindrical segment being interposed between spire s of said guidewire.

8. The device of claim 4 wherein said segment of guidewire comprises a an axially bored cylinder having an outer diameter substantially equal to an outer diameter of said spires, said axially bored cylinder sealingly engaging said core wire.

9. The device of claim 4, wherein: spaces between crests of said spires are sealed with sealing means to form with crests of said spires said substantially even surface, and spaces between said spires and said core wire is sealed with said sealing means.

10. The device of claim 4, wherein: said segment of guidewire comprises a tubular coating of said spires, said coating being interiorly sealed to passage of air.

11. The device of claim 1 further comprising means for prevention of injection of air into said blood vessel upon said advancing of said guidewire into the interior of the blood vessel.

12. The device of claim 11 wherein said means for prevention of injection of air into said blood vessel comprises an opening for escape of air, said air being forced through said opening by said self-propelling means advancing said guidewire, 13. The device of claim 11 wherein said means for prevention of injection of air into said blood vessel comprises said means for sealingly engaging said guidewire, and said segment of guidewire, said segment of guidewire being interiorly sealed to passage of air.

14. The device of claim 1 further comprising: gripping means engaging said guidewire to advance said guidewire and disengaging from said guidewire upon entry of said guidewire into said blood vessel.

15. The device of claim 1 wherein said self-propelling means advances said guidewire via gripping means having at least two opposite ridges engaging between said spires of said guidewire.

16. The device of claim 14 wherein said gripping means are slideably mounted within a chamber constructed with a restrained segment continuing into a contiguous expanded segment, said gripping means being centripetally constrained to engage said guidewire while said gripping means is sliding within said restrained segment of said chamber and being allowed to expand to disengage said guidewire upon entry of said gripping means into said expanded segment of said chamber.

17. The device of claim 1 wherein a segment of said guidewire is mounted within said hollow needle prior to said blood vessel penetration by said needle.

18. A guidewire placement device for insertion of a guidewire into the interior of a blood vessel comprising:

a hollow needle, a vacuum chamber for vacuum pressure said vacuum chamber having means for sealingly engaging a guidewire which is slidable within said hollow needle, said guidewire having at least one segment adapted to maintain said vacuum pressure within said vacuum chamber, said vacuum pressure being subjectable to a change upon blood vessel penetration by said needle and self-propelled means for advancing said guidewire into the interior of said blood vessel upon said change of vacuum pressure.

19. A guidewire placement device for insertion of a guidewire into the interior of a body cavity comprising:

a hollow needle, a vacuum chamber for vacuum pressure said vacuum chamber having means for sealingly engaging a guidewire which is slidable within said hollow needle, said guidewire having at least one segment adapted to maintain said vacuum pressure within said vacuum chamber, said vacuum pressure being subjectable to a change upon body cavity penetration by said needle and self-propelled means for advancing said guidewire into the interior of said body cavity upon said change of vacuum pressure.

* * * * *